United States Patent [19]

Donahue et al.

[11] Patent Number: 5,637,876

[45] Date of Patent: Jun. 10, 1997

[54] RADIATION DOSIMETRY METHOD AND APPARATUS

[75] Inventors: J. Michael Donahue, Oakland, N.J.; David F. Lewis, Monroe, Conn.; Henry Seiwatz, Wayne, N.J.; Carl A. Listl, New Hyde Park, N.Y.

[73] Assignee: ISP Investments Inc., Wilmington, Del.

[21] Appl. No.: 554,540

[22] Filed: Nov. 7, 1995

[51] Int. Cl.$^6$ ........................................ G01J 1/02
[52] U.S. Cl. ........................ 250/474.1; 250/473.1; 250/472.1
[58] Field of Search .................... 250/474.1, 473.1, 250/472.1, 580, 484.3, 484.4, 252.1

[56] References Cited

U.S. PATENT DOCUMENTS

| | | | |
|---|---|---|---|
| 4,454,421 | 6/1984 | Tanaka et al. | 250/474.1 |
| 4,757,201 | 7/1988 | Kanter | 250/337 |
| 4,913,881 | 4/1990 | Evers | 422/56 |
| 5,051,597 | 9/1991 | Lewis et al. | |
| 5,084,623 | 1/1992 | Lewis et al. | |

*Primary Examiner*—David P. Porta
*Assistant Examiner*—Richard Hanig
*Attorney, Agent, or Firm*—R. Neil Sudol; Jules Goldberg; Joshua J. Ward

[57] ABSTRACT

A method for determining a level of exposure to radiation utilizes a radiation dosimeter comprising a substrate provided with a radiation sensitive layer or patch having an optical density which varies in accordance with the degree of radiation exposure. In addition, the substrate is provided with optically readable coding which identifies encoded mathematical parameters for enabling an automated calculation of dosage from a detected post-exposure optical density of the radiation sensitive material. The method comprises the step of optically measuring the optical density of the layer of radiation sensitive material prior to exposure thereof to radiation. In addition, the coding on the dosimeter substrate is scanned to automatically determine the encoded mathematical parameters. The method further comprises the steps of exposing the radiation sensitive layer to radiation and optically measuring a post-exposure optical density of the layer of radiation sensitive material. Subsequently, from the pre-exposure optical density, the post-exposure optical density, and the mathematical parameters and in accordance with a predetermined mathematical algorithm, a quantitative radiation dose to which the layer of radiation sensitive material was exposed is automatically computed. Preferably, the computed quantitative radiation dose is automatically indicated on a display. Each dosimeter may be provided with a unique identification code encoded in the bar coding on the dosimeter substrate, to enable memory storage of preexposure optical densities for multiple dosimeters. A lookup table may be stored in memory for enabling correction of computed optical densities where the post-exposure densities are measured at different times intervals after exposure.

25 Claims, 2 Drawing Sheets

RADIATION DOSIMETRY METHOD AND APPARATUS

BACKGROUND OF THE INVENTION

This invention relates to a radiation dosimetry method and associated devices for carrying out the method. More particularly, this invention relates to a method and associated apparatus for quantitatively determining, in a convenient and timely manner, a dose of radiation applied to a patient or other subject.

In facilities where radioactive materials are used, for example, in hospitals where cancer patients receive radiation treatments or in blood banks where blood products are irradiated, various methods are used to quantitatively determine the radiation dose. The methods practiced include the use of thermoluminescent dosimeters (TLD's), ionization-type radiation detectors, photographic film, and radiochromic materials. TLD's are inconvenient because they require a complicated and time-consuming read-out process. Ionization-type radiation detectors are awkward and unwieldy and require a complicated setup. Photographic film requires a time-consuming chemical processing procedure before read-out. Radiochromic materials are inconvenient in current practice because the calculation of the dose requires a complex sequence of steps, subject to operator error.

SUMMARY OF THE INVENTION

An object of the present invention is to provide a new dosimetry methodology which is easy to use and less cumbersome than conventional techniques. Another object of the present invention is to provide such a methodology wherein quantitative dose information is available almost immediately after irradiation.

A further, more particular, object of the present invention, is to provide a dosimetry method wherein the user or operator does not have to calibrate the dosimetry medium or calculate the dose.

Yet another object of the present invention is to provide a dosimeter and a dose reader instrument which co-function to implement a dose determination. More particularly, it is desired to provide a dose reader which cooperates with dosimeters of different sensitivities, whereby the dose reader can be used for different applications having respectively divergent ranges of dosage.

A radiation dosimeter, exemplarily for use in determining a level of radiation to which a patient is subjected during radiation treatment, comprises, in accordance with the present invention, a substrate provided with a layer of radiation sensitive material. The radiation sensitive material has an optical density which varies systematically in accordance with the degree of radiation exposure. In addition, the substrate is provided with optically readable coding which identifies encoded mathematical parameters for enabling an automated calculation of dosage from a detected post-exposure optical density (or change in optical density) of the radiation sensitive material. As described in detail hereinafter, where the post-exposure optical density varies as a linear function of the amount of radiation exposure, the mathematical parameters include a slope parameter and a y-intercept parameter. Of course, depending in part on the nature of the radiation sensitive material and its mode of application to the dosimeter, a different quantitative relationship such as a higher order polynomial function may describe the variation of the radiation dose in accordance with the post-exposure optical density or change in optical density of the radiation sensitive material.

The dosimeter may take the form of a card or a flexible substrate which is positionable on the patient or other irradiation subject and which is also positionable in, or slidable through a slot in, a dose reader, described below. Preferably, the coding on the substrate takes the form of a bar code. In that case, the coding and the optical density of the exposed layer of radiation sensitive material may be read by the same dose reader instrument. The bar coding and the reflection intensity of the radiation sensitive layer may be sensed during a sliding of the dosimeter through a slot on the dose reader instrument. Alternatively, movable optical elements may be provided for reading the bar code information and measuring the optical density of the radiation sensitive layer while the dosimeter is held in a slot or recess on the dose reader instrument.

A dose reader instrument, for use with the dosimeter in measuring a radiation level to which a patient or other object is subjected, comprises, in accordance with the present invention, an optical sensor for sensing a range of variable optical densities on a substrate. The sensor includes or is connected to measurement componentry for determining an optical density of the layer of radiation sensitive material on the substrate. The dose reader further comprises a decoder operatively connected to the optical sensor for decoding the mathematical parameters encoded in the optically readable coding on the substrate. A computer is operatively connected to the measurement componentry and the decoder for computing, according to a predetermined mathematical function including the parameters determined from the coding on the substrate by the decoder, a quantitative radiation dose to which the layer of radiation sensitive material was exposed. A display or other communicating component (such as speech synthesis circuitry) is operatively connected to the computer for communicating the computed quantitative radiation dose to an operator.

The dose reader may include a frame and a holder such as a slot or recess provided on the frame for at least temporarily positioning the substrate at a pre-established distance from to the optical sensor during measurement of the optical density of the radiation sensitive layer on the substrate, while the optical sensor may include a light source and a photocell fixed to the frame.

According to another feature of the present invention, the dose reader further comprises a timer operatively coupled to the computer for enabling the computation of the quantitative radiation dose only upon the lapse of a preset interval after exposure of the layer of radiation sensitive material to radiation. Alternatively, the timer may measure the time interval between the exposure of the radiation sensitive material to radiation and the measurement of the post-exposure optical density of the radiation sensitive layer on the dosimeter. In that event, the difference between the measured interval and a preset time period determines a modification amount or adjustment factor to be applied to a calculated radiation dose to derive a final computed radiation dose. As discussed above with respect to the structure of the dosimeter, where the radiation level to which a subject is exposed is linearly related to the change in the optical density of the exposed layer of radiation sensitive material, the mathematical parameters encoded on the dosimeter include a slope parameter and a y-intercept parameter. The predetermined mathematical function used in computing the level of radiation exposure is $[\log[I(0)-D]\log[I(s)-D]-b]/m$ where D is a premeasured background intensity determined for the instrument during production and assembly, m is the slope parameter, b is the y-intercept parameter, $I(0)$ is a sensed pre-exposure reflection intensity of the layer of radiation sensitive material, I(s) is a sensed post-exposure reflection intensity of the layer of radiation sensitive material, log[I(0)-D] is proportional to a pre-exposure optical density of the layer of radiation sensitive material, log[I(s)-D] is proportional to a post-exposure optical density of the layer of radiation sensitive material, and [log[I(0)-D]-log[I(s)-D]] is a measured optical density change in the layer of radiation sensitive material.

Where another mathematical function describes the relationship between post-exposure optical density of a radiation sensitive dosimeter layer and the degree of irradiation, different mathematical parameters are encoded on the dosimeter, e.g., in a bar code. The principle underlying the invention is that the calibration information pertaining to the relationship between a post-exposure optical density of a radiation sensitive dosimeter layer and the degree of irradiation is encoded on the dosimeter itself, thereby enabling automatic computation of the radiation dosage from a measured optical density change.

A method for determining a level of exposure to radiation in accordance with the present invention utilizes the radiation dosimeter described above. The method comprises the step of optically measuring the pre-exposure optical density of the layer of radiation sensitive material. In addition, the coding on the dosimeter substrate is scanned to automatically determine the encoded mathematical parameters. Generally, after measurement of the pre-exposure optical density of the radiation sensitive layer, the dosimeter is placed on a subject to be irradiated. The method further comprises the steps of then exposing the radiation sensitive layer (and the subject) to radiation and subsequently optically measuring a post-exposure optical density of the radiation sensitive layer. Then, from the pre-exposure optical density, the post-exposure optical density, and the mathematical parameters and in accordance with a predetermined mathematical algorithm, a quantitative radiation dose to which the layer of radiation sensitive material was exposed is automatically computed. Preferably, the computed quantitative radiation dose is automatically indicated on a display.

The scanning of the coding to determine the mathematical parameters is performed prior to exposure of the layer of radiation sensitive material to radiation. However, the scanning of the parametric coding and the determination of the mathematical parameters may be implemented later, for example, at the time the post-exposure optical density of the radiation sensitive material is undertaken.

The optical density of the layer of radiation sensitive material may be measured by sensing a reflection (or transmission) intensity of the layer. The optical density is related logarithmically to the sensed reflection (or transmission) intensity. Where the reflection intensity is sensed, a reflection densitometer may be used.

It is within the contemplation of the present invention that a single subject may be provided with more than one dosimeter prior to an irradiation procedure. In that event, it is advantageous if the substrates of the dosimeters are provided with additional optically readable coding identifying the respective dosimeters and enabling association of measured pre-exposure optical densities (or reflection/transmission intensities) with the proper dosimeters for computing respective quantitative radiation doses. Generally, the measured pre-exposure densities (or reflection/transmission intensities) are automatically stored by the dose reader instrument in association with the read dosimeter identities. For example, memory locations for the measured pre-exposure densities (or reflection/transmission intensities) may be determined by the dosimeter identities. Alternatively, both the measured pre-exposure densities and the respective dosimeter identities may be stored at the same locations. Upon reading a dosimeter identity from a substrate coding during a post-exposure optical density measurement, the computer or microprocessor scans the memory for the previously measured pre-exposure optical density (or reflection/transmission intensity) for that dosimeter. Then the pre-exposure optical density and the post-exposure optical density for the same dosimeter are used in calculating the radiation dose experienced by that dosimeter.

Pursuant to another aspect of the present invention, the scanning of the bar code may be effectuated during a movement of the dosimeter through a slot on a dose reader instrument. Then optical measuring of the optical density of the layer of radiation sensitive material may be performed by operating a reflection densitometer apparatus.

After the determination of the pre-exposure optical density of the radiation sensitive layer, the substrate is removed from the dose reader instrument and then placed on a subject, prior to the exposure of the radiation sensitive material to radiation. After exposure and prior to optical scanning of the layer to determine the second optical density, the substrate is temporarily placed again at the pre-established location on, or slot in, the dose reader instrument.

In accordance with the present invention, where the predetermined mathematical function is linear, the radiation dose is computed according to the function $[\log[I(0)-D]\log[I(s)-D]-b]/m$ where D is a premeasured background intensity, m is a slope parameter, b is a y-intercept parameter, I(0) is a sensed pre-exposure reflection intensity of the radiation sensitive layer, I(s) is a sensed post-exposure reflection intensity, $\log[I(0)-D]$ is proportional to a pre-exposure optical density of the layer of radiation sensitive material, $\log[I(s)-D]$ is proportional to a post-exposure optical density of the layer of radiation sensitive material, and $[\log[I(0)-D]-\log[I(s)-D]]$ is a measured optical density change in the layer of radiation sensitive material. This linear function pertains when the post-exposure measurement is performed a known or predetermined interval after the irradiation. If the measurement takes place at a different time after exposure of the dosimeter, the same function may be used to compute a dose value which is then modified automatically by an amount determined by the difference between the preset interval and the actual post-exposure time that the measurement is made. The modification amount or factor may be taken from a table of experimentally predetermined values stored, for example, in a computer memory.

A method for determining a level of exposure to radiation, in accordance with a broader conceptualization of the present invention, utilizes a radiation dosimeter including a layer of radiation sensitive material on a substrate, the radiation sensitive material having an optical density which varies systematically in accordance with a degree of radiation exposure. The method includes (I) scanning the substrate to determine calibration information relating to the layer of radiation sensitive material, (ii) exposing the layer of radiation sensitive material to radiation, (iii) optically measuring the post-exposure optical density of the radiation sensitive layer, and (iv) automatically computing, from the calibration information and the post-exposure optical density and in accordance with a predetermined mathematical algorithm, a quantitative radiation dose to which the radiation sensitive layer was exposed. Generally, it is contemplated that the pre-exposure optical density of the radiation sensitive layer is also measured and subsequently used in computing the radiation dose. It may be possible eventually to premeasure the pre-exposure optical density (e.g., at the factory) and encode the measured pre-exposure optical density in the bar coding on the dosimeter.

Where the radiation dosimeter also includes an optically readable coding which identifies encoded mathematical parameters for use in computing the radiation dose, the scanning of the substrate includes a reading of the mathematical parameters from the coding. The mathematical parameters are, for example, constants in an experimentally determined functional relationship used in deriving a quantitative value for the amount of radiation exposure. As discussed above, the predetermined functional relationship may be the linear function $[\log[I(0)-D]-\log[I(s)-D]-b]/m$ where D is a premeasured background intensity, m is a slope parameter included in the mathematical parameters, b is a y-intercept parameter included in the mathematical parameters, $I(0)$ is a sensed pre-exposure reflection intensity of the layer of radiation sensitive material, $I(s)$ is a sensed post-exposure reflection intensity, $\log[I(0)-D]$ is proportional to a pre-exposure optical density of the layer of radiation sensitive material, $\log[I(s)-D]$ is proportional to a post-exposure optical density of the layer of radiation sensitive material, and $[\log[I(0)-D]-\log[I(s)-D]]$ is a measured optical density change in the layer of radiation sensitive material.

Preferably, the optical measuring of the post-exposure optical density of the radiation-sensitive material is performed only after a pre-determined interval has elapsed after exposure of the layer to radiation. However, if circumstances require measurement of the post-exposure optical density at a different time, the difference between the actual measurement time and the preferred time may be used to determine a modification amount or factor, e.g., selected from a table of experimentally predetermined values, for adjusting the result of the above-described computation. Such circumstances might occur, for example, where the use of several dosimeters on the irradiation subject necessarily results in at least one post-exposure optical measurement made before or after the preset interval has expired (assuming the use of the same dose reader).

A radiation dose determination method in accordance with the present invention is easier to use than conventional methods and provides a virtually real time determination of radiation dosage. The ease of use and the practicable immediacy of results are enabled in part by the automatic calibration of the dosimetry medium, i.e., the radiation sensitive layer on the dosimeter, at the time of the radiation. In contrast to other radiation level determination procedures, such as those dosage measurement using other radiochromic materials, the user does not have to expend effort in calibrating the dosimetry medium. Furthermore, the present technique is much quicker and easier to use than thermoluminescent dosimeters, which require extensive effort and time to read out the results.

In practice, each manufactured batch of radiation sensitive material characterized by a linear mathematical function may be tested to determine the slope and intercept parameters which define the linear optical sensitivity of the radiation sensitive material. The slope and intercept parameters are encoded on each dosimeter for use by the computer or microprocessor of the dose reader instrument in calculating a dose level from the change in the optical density of the radiation sensitive layer on the particular dosimeter. Several different types of dosimeters may be provided, having respective sensitivities, and thus respective calibration parameters, for use in different applications.

The incorporation of calibration information into the dosimeters enables the use of a standardized dose reader instrument, regardless of the application.

DETAILED DESCRIPTION

Figure 1:
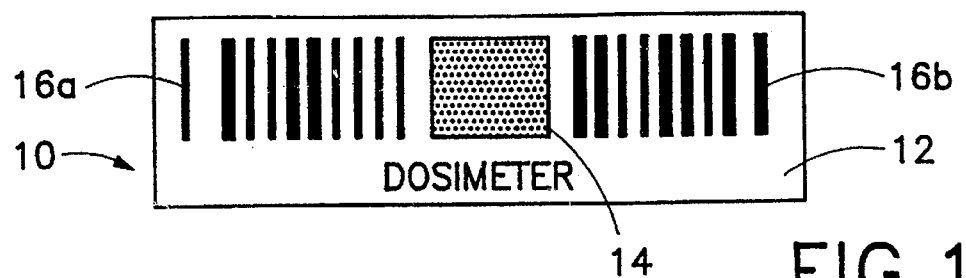
FIG. 1 is a plan view of a dosimeter or radiation measurement patch in accordance with the present invention.

As illustrated in FIG. 1, a radiation dosimeter 10 comprises a planar substrate or carrier 12 which can be positioned on a patient or other person or object to which radiation is applied. Dosimeter 10 is used, as discussed in detail hereinafter, for determining a level of radiation to which a patient, person or object is subjected during a radiation treatment procedure. Substrate 12 is provided with a patch or layer 14 of radiation sensitive material. The radiation sensitive material has an optical density which varies systematically, e.g., linearly, in accordance with the amount of radiation exposure. In addition, substrate 12 is provided with one or more optically readable bar codes 16a, 16b which identify encoded mathematical parameters, particularly a slope and an intercept of a linear equation or expression. These encoded mathematical parameters enable an automated calibration of the sensitivity of the particular radiation sensitive patch or layer 14 of dosimeter 10 and concomitantly enable an automated calculation of radiation dosage from a detected change in optical density of the radiation sensitive material of patch 14.

Although FIG. 1 shows two bar codes 16a and 16b, it may be preferable, for example, for space reasons, to provide a single bar code, i.e., a single series of bars of varying widths. Moreover, the bar coding 16a, 16b on substrate 12 may include a unique identification of the respective dosimeter, enabling a seriatim measurement of several pre-exposure optical densities and storage of the measured densities in memory for later selective recall. This option is particularly useful where several dosimeters 10 are applied to the same subject and exposed during the same irradiation process.

Figure 2:
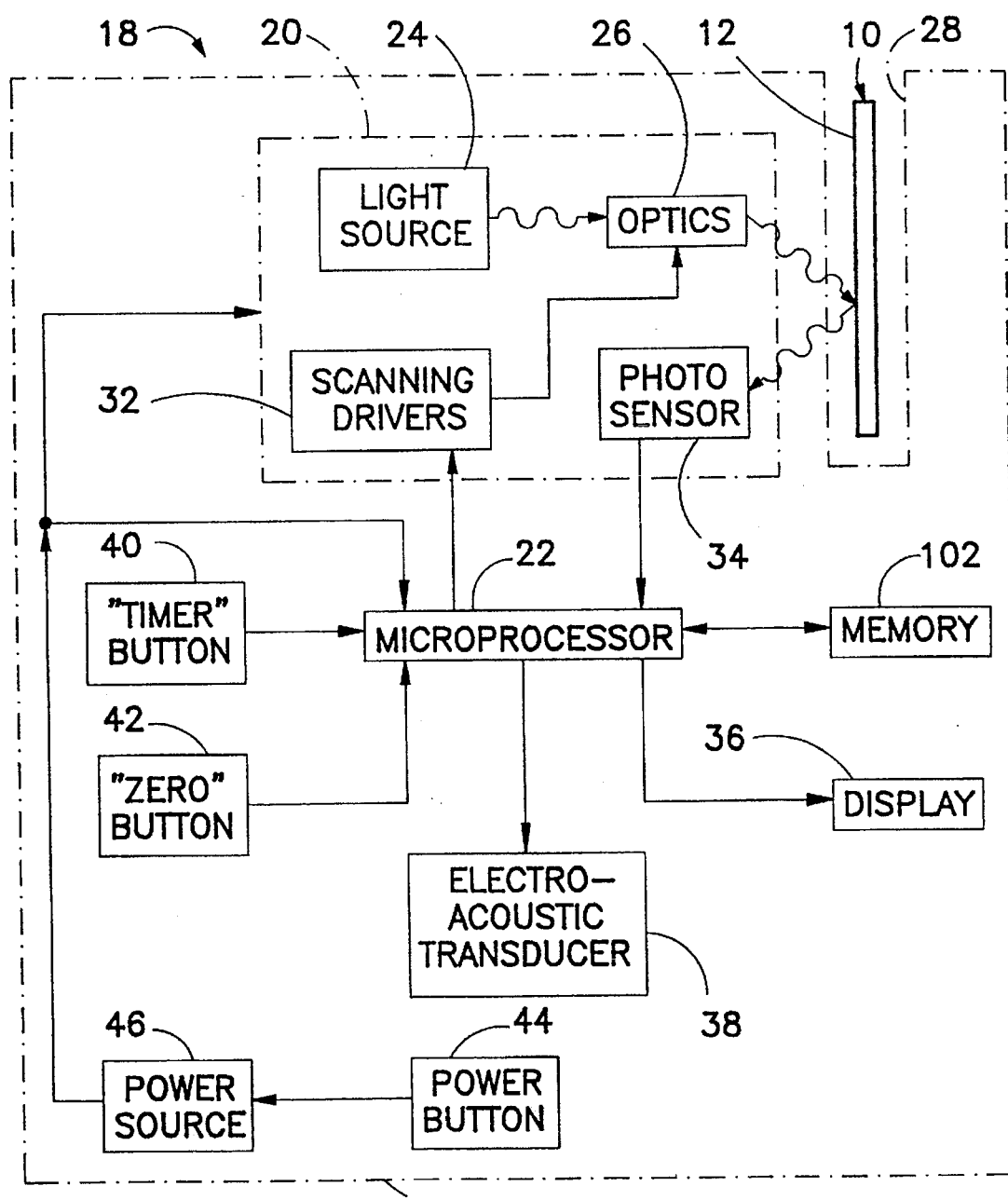
FIG. 2 is a block diagram of a dose reader used to determine a radiation dosage received by the dosimeter of FIG. 1.

Prior to and after exposure of patch 14 to radiation, the optical density of the radiation sensitive material of the patch is measured by a dose reader 18, illustrated diagrammatically in FIG. 2. Dose reader 18 comprises an optical scanner or reflection densitometer 20 for sensing a range of variable reflection intensities at a multiplicity of different locations on substrate 12. The optical scanner or scanning reflection densitometer 20 cofunctions with a microprocessor 22 to determine or measure an optical density of radiation sensitive patch 14 and to decode the mathematical parameters encoded in bar codes 16a and 16b. A measured optical density is logarithmically related to a sensed reflection intensity, as indicated in greater detail hereinafter.

Optical scanner or scanning reflection densitometer 20 includes a light source 24 which produces electromagnetic radiation of a predetermined intensity and range of wavelengths. The electromagnetic radiation from light source 24 is directed by optical elements 26 to dosimeter 10, which is held in a slot 28 in a frame or casing 30. Optical elements 26 are controlled by scanning drivers 32 in turn controlled by microprocessor 22. Optical scanner or scanning reflection densitometer 20 further includes a photocell or optical sensor element 34 for detecting radiation reflected from dosimeter 10. Photocell 34 is operatively connected to microprocessor 22 for feeding thereto an electrical signal identifying the intensity of the reflection from different points on dosimeter 10.

In accordance with the signal from photocell 34, microprocessor 22 acts to determine the optical density of radiation sensitive patch 14 and to decode the parametric information encoded in bar codes 16a and 16b. As discussed in detail hereinafter, microprocessor 22 also functions to compute a quantitative value for a radiation dose from the decoded parameters and the measured optical density of radiation sensitive patch 14, both before and after exposure to radiation.

As further illustrated in FIG. 2, dose reader 18 further includes a display 36 or other communicating component (such as speech synthesis circuitry—not illustrated) which is operatively connected to microprocessor 22 for communicating the computed quantitative radiation dose to an operator. Dose reader 18 additionally includes an electroacoustic transducer or speaker component 38 connected to an output of microprocessor 22 for generating an alert sound in response to a signal from the microprocessor.

A "timer" button 40 and a "zero" button 42 provided on frame 30 are connected to microprocessor 22 for inducing a counting operation and a pre-exposure optical density measurement operation by the microprocessor, respectively. More specifically, timer button 40 is operatively coupled to microprocessor 22 for enabling the post-exposure optical density measurement and computation of the quantitative radiation dose only upon the lapse of a known or predetermined fixed interval after exposure of the layer of radiation sensitive material to radiation.

The radiation level to which a subject is exposed is systematically, e.g., linearly, related to the change in optical density of the exposed radiation sensitive patch 14. A predetermined linear mathematical function used by microprocessor 22 in computing the level of radiation exposure is $[\log[I(0)-D]-\log[I(s)-D]-b]/m$ where D is a premeasured background intensity determined for a particular dose reader 18 during production and assembly, m is the slope parameter encoded in bar code 16a or 16b, b is the y-intercept parameter encoded in bar code 16b or 16a, I(0) is a sensed pre-exposure reflection intensity of radiation sensitive patch 14, and I(s) is a sensed post-exposure reflection intensity of patch 14, $\log[I(0)-D]$ is proportional to a pre-exposure optical density of patch 14, $\log[I(s)-D]$ is proportional to a post-exposure optical density of patch 14, and $[\log[I(0)-D]-\log[I(s)-D]]$ is a measured optical density change of patch 14.

As additionally illustrated in FIG. 2, dose reader 18 includes a power button 44 on frame 30. Power button 44 induces the supply of power from a source 46 to various components of the dose reader, including microprocessor 22 and optical scanner or scanning reflection densitometer 20.

Figure 3:
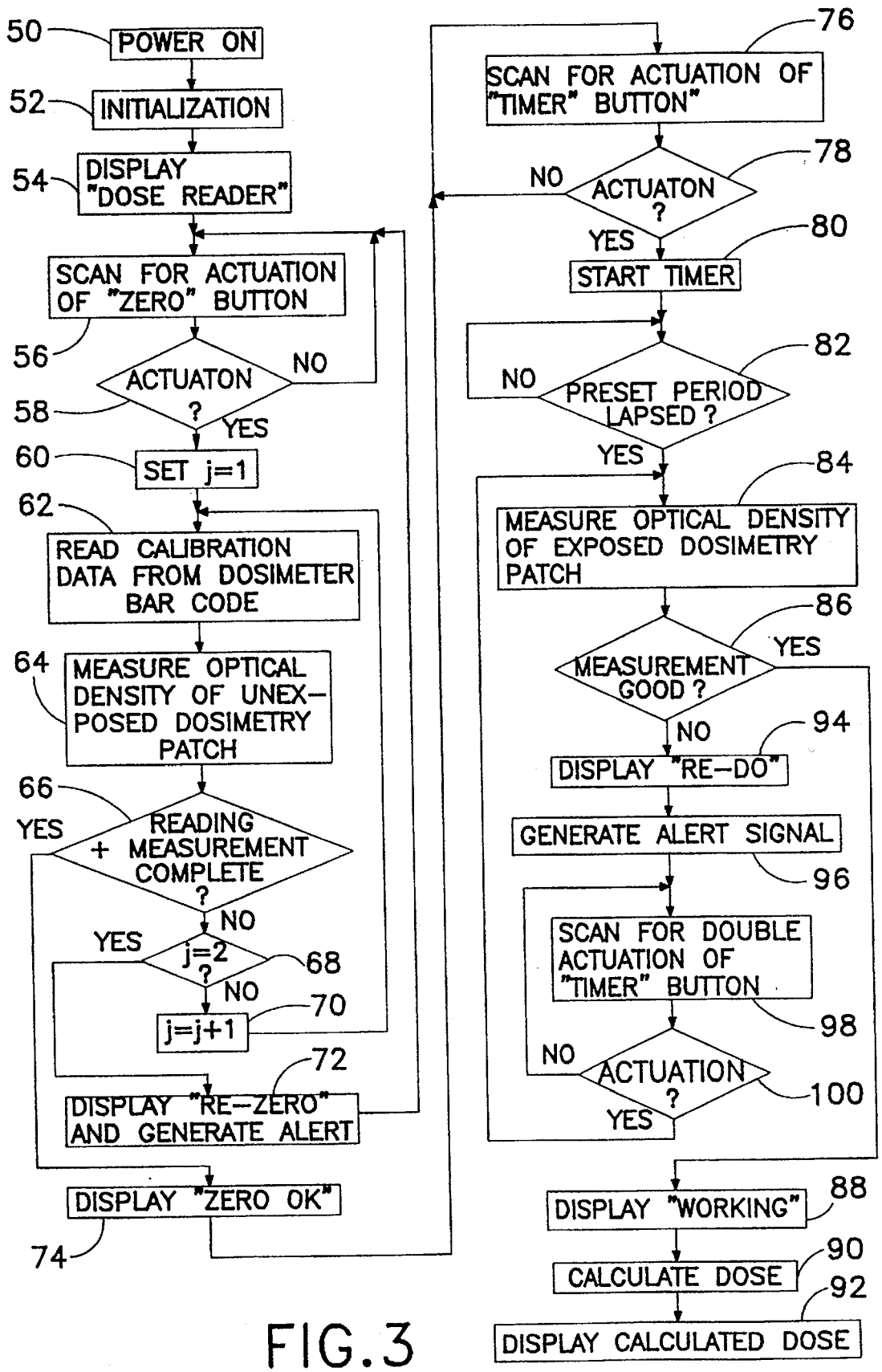
FIG. 3 is a flow chart diagram showing steps in the operation of a microprocessor included in the dose reader of FIG. 2.

FIG. 3 diagrammatically depicts a dosimetry method as controlled by microprocessor 22. Upon a receiving a signal from power button 44 in a step 50, microprocessor 22 undergoes a self-initialization sequence 52 and subsequently energizes display 36, in a step 54, to show the words "Dose Reader" Microprocessor 22 then undertakes a scan 56 to determine whether "zero" button 42 has been actuated. Upon determining at a decision junction 58 that "zero" button 42 has been pressed, microprocessor 22 allots a value of 1 to a temporary parameter j in a step 60 and then cooperates with optical scanner or scanning reflection densitometer 20 in a step 62 to read the calibration data (m, b) for a particular dosimeter 10 from the bar codes 16a and 16b thereon. In addition, microprocessor 22 coacts with optical scanner or scanning reflection densitometer 20 in a step 64 to sense a pre-exposure reflection intensity and measure a corresponding pre-exposure optical density of radiation sensitive patch 14. Of course, the unexposed densitometer 10 has been inserted into (or slid through) slot 28 prior to (or during) the scanning of the densitometer by optical scanner or scanning reflection densitometer 20.

Upon determining at a decision junction 66 that reading and measurement steps 62 and 64 have not been successfully completed, microprocessor 22 inquires at 68 whether temporary parameter j is equal to 2. If not, parameter j is incremented in a step 70 and microprocessor 22 again undertakes reading and measurement steps 62 and 64. If microprocessor 22 has already made two attempts at reading bar codes 16a and 16b and measuring the optical density of radiation sensitive patch 14, the microprocessor energizes display 36 to show the word "ReZero" and generates an audible alert signal via electroacoustic transducer 38 (step 72). Dose reader 18 may also be provided with an additional visual indicator such as a red light (not 25 shown) for alerting a user that dose reader 18 is unable to calibrate or read a dosimeter 10 in slot 28. The dosimeter 10 may be reinserted or another dosimeter card may be tried.

Once microprocessor 22 determines the particular calibration parameters m and b from bar codes 16a and 16b on dosimeter 10, as ascertained at decision junction 66, the microprocessor activates display 36 to display the term "Zero OK" in a step 74 and then scans, in a step 76, for an actuation of timer button 40. An actuation of button 40 means that dosimeter 10 has been removed from slot 28, placed on a subject and irradiated. The user should press button 40 as soon as irradiation has ceased. The user then places the exposed dosimeter 10 back into slot 28.

Upon an actuation of "timer" button 40, detected by microprocessor 22 in an inquiry 78, the microprocessor starts an internal clock running in a step 80. After the passage of a preestablished interval or period of time, monitored by microprocessor 22 in an inquiry 82, the microprocessor coacts with optical scanner or scanning reflection densitometer 20 in a step 84 to measure the optical density of the exposed radiation sensitive patch 14. If the measurement is good, as determined by microprocessor 22 at a decision junction 86, the microprocessor activates display 36 in a step 88, calculates the radiation dose in a step 90 and finally displays the calculated dosage in a step 92. As discussed above, microprocessor 22 computes the level of radiation exposure from the equation or expression $[\log[I(0)-D]-\log[I(s)-D]-b]/m$ where D is a premeasured background intensity determined for a particular dose reader 18 during production and assembly, m is the slope parameter encoded in bar code 16a or 16b, b is the y-intercept parameter encoded in bar code 16a or 16b, I(0) is a pre-exposure reflection intensity sensed in step 64, and I(s) is a post-exposure reflection intensity sensed in step 84, while $\log[I(0)-D]$ is proportional to a pre-exposure optical density of the layer of radiation sensitive material measured in step 64, $\log[I(s)-D]$ is proportional to a post-exposure optical density of the layer of radiation sensitive material measured in step 84, and $[\log[I(0)-D]-\log[I(s)-D]]$ is an optical density change in the layer of radiation sensitive material.

If the measurement of the post-exposure optical density of radiation sensitive patch 14 is unsatisfactory, as determined at decision junction 86, microprocessor 22 energizes display 36 in a step 94 to show the word "Re-do" and energizes electroacoustic transducer 38 in a step 96 to issue an audible alert signal. The microprocessor then waits for a double actuation of timer button 40 (step 98). If the timer button is pressed twice, as determined at 100, microprocessor 22 undertakes immediately another measurement of the optical density of the exposed radiation sensitive patch 14 of the dosimeter 10 in slot 28.

In performing a dosimetry procedure using dosimeter 10 and dose reader 18, the reflectivity of radiation sensitive patch 14 is optically measured prior to exposure thereof to radiation to thereby determine a pre-exposure optical density of patch 14. In addition, bar codes 16a and 16b on dosimeter substrate 12 are scanned to automatically determine the encoded mathematical parameters m and b. Subsequently, after exposure of the dosimeter to radiation and upon lapse of a preset period after the exposure, the post-exposure optical density of radiation sensitive patch 14 is measured optically. Then, in accordance with a predetermined mathematical algorithm incorporating the pre-exposure optical density, the post-exposure optical density, and the decoded or read mathematical parameters m and b, microprocessor 18 automatically computes a quantitative value of the radiation dose to which a subject and the dosimeter 10 were exposed. The computed dose is automatically displayed in virtual real time, i.e., shortly after the irradiation procedure.

Waiting a predetermined period after the termination of an irradiation procedure before measuring the optical density of the exposed patch 14 permits completion of the chemical reactions in the radiation sensitive material induced by the exposure to radiation. The radiation sensitive material of patch 14 is well known in the industry.

Preferably, the reading of bar codes 16a and 16b is performed prior to exposure of the dosimeter 10 to radiation. However, the scanning of the parametric codes 16a and 16b and the associated determination of the mathematical parameters m and b may be implemented later, for example, at the time the post-exposure optical density of radiation sensitive patch 14 undertaken.

In an alternative dosimetry method, reflection densitometer 20 (FIG. 2) is a simple densitometer, without the scanning capability provided by scanning drivers 32 and adjustable optics 26. Thus, in dose reader 18, scanning drivers 32 may be omitted. To enable reflection densitometer 20 to sense bar coding 16a and 16b for a determination of mathematical parameters m, b, a user simply slides dosimeter 10 through slot 28, in the same manner that one slides, for example, a credit card through a slot past a magnetic reader. The measurement of the optical density of patch or layer 14 may be made during the same swiping motion of the dosimeter 10. Alternatively, dosimeter 10 may be temporarily left in slot 28 during the measurement of optical density.

It is to be noted that the dosimetry method and dose reader 18 may be modified to enable measurement of the post-exposure optical density of radiation sensitive patch 14 at different times after irradiation has ceased. For example, where the function $[\log[I(0)-D]-\log[I(s)-D]-b]/m$ is used to calculate the radiation dose from a post-exposure reflection intensity measured a predetermined interval after exposure, the result computed from this expression may be automatically adjusted by microprocessor 22 (FIG. 2) to derive the actual radiation dose when the post-exposure reflection intensity is measured at a different time, i.e., before or after the predetermined post-exposure interval has elapsed. Accordingly, timer button 40 may be used to start a clock internal to microprocessor 22 by which the microprocessor measures the time from the cessation of irradiation to the measurement of optical density. The difference between the measured interval and the preset time period determines a modification amount or adjustment factor to be applied to the calculated radiation dose to derive a final actual radiation dose. To that end, microprocessor 22 is connected to a memory 102 provided in dose reader 18 for storing a table of modification amounts or adjustment factors.

It is advantageous if bar coding 16a, 16b on substrate 12 includes a unique identification of the respective dosimeter 10. This enables, for instance, the utilization of several dosimeters on the same subject during the same irradiation procedure. The pre-exposure optical densities of the radiation sensitive patches 14 of the respective dosimeters 10 are measured in seriatim and stored by microprocessor 22 in memory 102. Later, upon the sliding of a particular exposed dosimeter 10 through slot 28 and the measurement of the post-exposure optical density of that dosimeter, microprocessor 22 accesses memory 102 and retrieves the respective pre-exposure optical density for use in computing the radiation dose experienced by the particular dosimeter 10. Generally, the measured pre-exposure densities are automatically stored by microprocessor 22 in association with the dosimeter identities read from coding 16a, 16b. Addresses in memory 102 for the measured pre-exposure densities may be determined by the dosimeter identities. Alternatively, both the measured pre-exposure densities and the respective dosimeter identities may be stored at the same locations. Of course, when only one dose reader is available for making multiple dose measurements pursuant to this procedure, the above-described table of modification amounts or adjustment factors is necessary.

Although the invention has been described in terms of particular embodiments and applications, one of ordinary skill in the art, in light of this teaching, can generate additional embodiments and modifications without departing from the spirit of or exceeding the scope of the claimed invention. For example, although the above description specifically discloses the sensing of bar coding 16a, 16b and the pre- and post-exposure optical densities of radiation sensitive patch 14 via a reflection densitometer apparatus, the same readings and measurements can be implemented via the transmission of optical energy through dosimeter 10. Accordingly, it is to be understood that the drawings and descriptions herein are proffered by way of example to facilitate comprehension of the invention and should not be construed to limit the scope thereof.

What is claimed is:

1. A radiation dosimeter, comprising:
   a substrate;
   a layer of radiation sensitive material on said substrate, said radiation sensitive material having an optical density which varies in accordance with a degree of radiation exposure of said radiation sensitive material;
   optically readable first coding disposed on said substrate, said coding identifying encoded mathematical parameters for enabling an automated calculation of radiation dosage from a detected change in optical density of said radiation sensitive material; and
   additional optically readable second coding on said substrate for uniquely identifying the dosimeter.

2. The dosimeter defined in claim 1, wherein said first coding is a bar coding.

3. The dosimeter defined in claim 2, wherein the mathematical parameters encoded in said first coding include a slope parameter.

4. The dosimeter defined in claim 3, wherein the mathematical parameters encoded in said first coding further include a y-intercept parameter.

5. A dose reader instrument comprising:

optical sensing means for sensing a range of variable optical densities on a substrate;

measuring means operatively connected to said optical sensing means for determining an optical density of a layer of radiation sensitive material on said substrate;

decoding means operatively connected to said optical sensing means for decoding mathematical parameters encoded in an optically readable coding on said substrate;

computing means operatively connected to said measuring means and said decoding means for computing, according to a predetermined mathematical function including a measured post-exposure value of said optical density and parameters determined from said coding by said decoding means, a quantitative radiation dose to which said layer of radiation sensitive material was exposed;

communicating means operatively connected to said computing means for communicating the computed quantitative radiation dose to an operator; and timing means operatively coupled to said computing means for enabling said computing means to compute said quantitative radiation dose only upon the lapse of a preset interval after exposure of said layer of radiation sensitive material to radiation.

6. The instrument defined in claim 5, further comprising a frame with a slot for enabling a sliding of said substrate past said optical sensing means at a pre-established distance from said optical sensing means.

7. The instrument defined in claim 6, wherein said optical sensing means includes a light source and a photocell fixed to said frame.

8. The instrument defined in claim 5 wherein said communicating means includes an optical display.

9. The instrument defined in claim 5 wherein said mathematical parameters include a slope parameter and a y-intercept parameter.

10. The instrument defined in claim 5 wherein said predetermined mathematical function is $[\log[I(0)-D]-\log[I(s)-D]-b]/m$ where D is a premeasured background intensity determined for the instrument during production and assembly, m is the slope parameter, b is the y-intercept parameter, $I(0)$ is a pre-exposure intensity of light emanating from said layer of radiation sensitive material prior to exposure thereof to radiation, $I(s)$ is a post-exposure intensity of light emanating from said layer of radiation sensitive material after exposure thereof to radiation, $\log[I(0)-D]$ is proportional to a pre-exposure optical density of said layer of radiation sensitive material, and $\log[I(s)-D]$ is proportional to said post-exposure optical density of said layer of radiation sensitive material.

11. The instrument defined in claim 5, further comprising (a) additional decoding means operatively connected to said optical sensing means for decoding a dosimeter identification code on said substrate and (b) memory means operatively connected to said additional decoding means and to said measuring means for storing a decoded dosimeter identification code for a selected dosimeter and a measured pre-exposure optical density of said selected dosimeter, said memory means being operatively connected to said computing means for providing said measured pre-exposure optical density to said computing means.

12. A method for determining a level of exposure to radiation, comprising:

providing a radiation dosimeter including a layer of radiation sensitive material on a substrate, said radiation sensitive material having an optical density which varies in accordance with a degree of radiation exposure, the radiation dosimeter also including an optically readable first coding disposed on said substrate, said first coding identifying encoded mathematical parameters, the radiation dosimeter being additionally provided with optically readable second coding uniquely identifying the dosimeter;

prior to exposure of said radiation sensitive material to radiation, optically measuring a first optical density of said layer of radiation sensitive material;

automatically reading said second coding to determine the identity of the dosimeter; and automatically storing said first optical density in electronically encoded form in a memory location associated with the determined identity of the dosimeter;

optically scanning said first coding to automatically determine said mathematical parameters;

after measuring said first optical density, exposing said layer of radiation sensitive material to radiation;

after exposure of said layer of sensitive material to radiation, optically measuring a second optical density of said layer of radiation sensitive material; and automatically computing, from said first optical density, said second optical density, and said mathematical parameters and in accordance with a predetermined mathematical algorithm, a quantitative radiation dose to which said layer of radiation sensitive material was exposed.

13. The method defined in claim 12 wherein the scanning of at least said first coding is performed prior to exposure of said layer of radiation sensitive material to radiation.

14. The method defined in claim 12 wherein measuring the optical density of said layer of radiation sensitive material includes operating a reflection densitometer apparatus to sense a reflection intensity.

15. The method defined in claim 14 wherein the scanning of at least said first coding is performed upon a passing of the dosimeter through a reader slot of a dose reader instrument.

16. The method defined in claim 12, further comprising the step, performed prior to the optical measuring of said first optical density, of at least temporarily positioning said substrate at a pre-established location in a dose reader instrument.

17. The method defined in claim 16 wherein said substrate is removed from said dose reader instrument and then placed on a subject prior to the exposure of said radiation sensitive material to radiation, said substrate being placed again at least temporarily at said pre-established location after exposure of said radiation sensitive material to radiation and prior to optical measuring of said second optical density.

18. The method defined in claim 12, further comprising automatically displaying the computed quantitative radiation dose.

19. The method defined in claim 12 wherein the step of measuring said first optical density includes the step of sensing a pre-exposure intensity of light emanating from said layer of radiation sensitive material, the step of measuring said second optical density including the step of sensing a post-exposure intensity of light emanating from said layer of radiation sensitive material, said predetermined mathematical function being $[\log[I(0)-D]-\log[I(s)-D]-b]/m$ where D is a premeasured background intensity, m is a slope parameter included in said mathematical parameters, b is a y-intercept parameter included in said mathematical parameters, I(0) is said pre-exposure intensity, I(s) is said post-exposure intensity, $\log[I(0)-D]$ is proportional to said first optical density, and $\log[I(s)-D]$ is proportional to said second optical density.

20. A method for determining a level of exposure to radiation, comprising:

providing a radiation dosimeter including a layer of radiation sensitive material on a substrate, said radiation sensitive material having an optical density which varies in accordance with a degree of radiation exposure of the radiation sensitive material;

scanning said substrate to determine calibration information relating to said layer of radiation sensitive material;

exposing said layer of radiation sensitive material to radiation;

after exposure of said layer to radiation, optically measuring a post-exposure optical density of said layer of radiation sensitive material;

automatically computing from said calibration information and said optical density and in accordance with a predetermined mathematical algorithm, a quantitative radiation dose to which said layer of radiation sensitive material was exposed;

measuring a time interval between exposing said layer of radiation sensitive material to radiation and measuring the post-exposure optical density of said radiation sensitive layer; and automatically modifying the computed quantitative radiation dose in accordance with a difference between the measured time interval and a preset interval.

21. The method defined in claim 20 wherein the radiation dosimeter also includes an optically readable coding disposed on said substrate, said coding identifying encoded mathematical parameters, the scanning of said substrate including a reading of said mathematical parameters from said coding, further comprising the step of optically measuring a pre-exposure optical density of said layer of radiation sensitive material, said pre-exposure optical density being used in the computation of said quantitative radiation dose in accordance with said predetermined mathematical algorithm.

22. The method defined in claim 21 wherein the step of measuring said pre-exposure optical density includes the step of sensing a pre-exposure reflection intensity of said layer of radiation sensitive material, the step of measuring said post-exposure optical density including the step of sensing a post-exposure reflection intensity of said layer of radiation sensitive material, said predetermined mathematical function being $[\log[I(0)-D]-\log[I(s)-D]-b]/m$ where D is a premeasured background intensity, m is a slope parameter included in said mathematical parameters, b is a y-intercept parameter included in said mathematical parameters, I(0) is said pre-exposure reflection intensity, I(s) is said post-exposure reflection intensity, $\log[I(0)-D]$ is proportional to said pre-exposure optical density, and $\log[I(s)-D]$ is proportional to said post-exposure optical density.

23. The method defined in claim 21 wherein the radiation dosimeter is provided with optically readable coding uniquely identifying the dosimeter, further comprising the steps of automatically reading said coding to determine the identity of the dosimeter and automatically storing said pre-exposure optical density in electronically encoded form in a memory location associated with the determined identity of the dosimeter.

24. A dose reader instrument comprising:

optical sensing means for sensing a range of variable optical densities on a substrate;

measuring means operatively connected to said optical sensing means for determining an optical density of a layer of radiation sensitive material on said substrate;

decoding means operatively connected to said optical sensing means for decoding mathematical parameters encoded in an optically readable coding on said substrate;

computing means operatively connected to said measuring means and said decoding means for computing, according to a predetermined mathematical function including a measured post-exposure value of said optical density and parameters determined from said coding by said decoding means, a quantitative radiation dose to which said layer of radiation sensitive material was exposed;

communicating means operatively connected to said computing means for communicating the computed quantitative radiation dose to an operator;

timing means operatively coupled to said computing means for measuring a time interval between exposure of said layer of radiation sensitive material to radiation and an operation of said measuring means to determine said post-exposure value of said optical density; and means operatively connected to said computing means for enabling a modification of the computed radiation dose in accordance with a difference between said interval and a preset interval.

25. The instrument defined in claim 24 wherein said means for enabling a modification of the computed radiation dose includes a table of modification values.

* * * * *